(12) United States Patent
Park et al.

(10) Patent No.: US 10,189,732 B2
(45) Date of Patent: Jan. 29, 2019

(54) ALGAL-SLUDGE GRANULE FOR WASTEWATER TREATMENT AND BIOENERGY FEEDSTOCK GENERATION

(71) Applicants: University of Massachusetts, Boston, MA (US); Michael F. Dolan, Belchertown, MA (US)

(72) Inventors: Chul Park, Amherst, MA (US); Sona Dolan, Belchertown, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/211,396

(22) Filed: Jul. 15, 2016

(65) Prior Publication Data

US 2016/0318782 A1    Nov. 3, 2016

Related U.S. Application Data

(63) Continuation of application No. PCT/US2015/012332, filed on Jan. 22, 2015.
(Continued)

(51) Int. Cl.
*C02F 3/32*       (2006.01)
*C02F 3/30*       (2006.01)
(Continued)

(52) U.S. Cl.
CPC .............. *C02F 3/325* (2013.01); *A01G 33/00* (2013.01); *C02F 3/006* (2013.01); *C12N 1/12* (2013.01);
(Continued)

(58) Field of Classification Search
CPC ........ C02F 3/325; C02F 3/006; C02F 3/1263; C02F 2305/06; C02F 2303/10;
(Continued)

(56) References Cited

U.S. PATENT DOCUMENTS 5,910,254 A  *  6/1999  Guelcher ................. C12N 1/02
                                                  209/164
6,199,317 B1 *  3/2001  Saiki ....................... A01G 33/00
                                                   47/1.4
(Continued)

OTHER PUBLICATIONS

USPTO, International Search Report for parent PCT/US15/012332, dated Jul. 10, 2015.
(Continued)

*Primary Examiner* — Fred Prince
(74) *Attorney, Agent, or Firm* — Schwegman Lundberg & Woessner, P.A.

(57) ABSTRACT

A granular or particulate composition of matter that includes algae and bacteria is described. The algal-sludge granules are generated by incubating a wastewater system with algae under specific quiescent conditions with illumination. Once the algal-sludge granules are present, it is no longer necessary to maintain quiescent conditions, and reaction with wastewater under stirred conditions is possible. The methods described include ab initio generation of the algal-sludge granules, use of the algal-sludge granules to remediate wastewater, and use of the algal-sludge granules to generate biomass. It is believed that the remediation of wastewater by algal-sludge granules will save the energy for wastewater treatment, recover the energy in wastewater in the form of biomass, and reduce the wastewater treatment carbon footprint.

20 Claims, 11 Drawing Sheets

Related U.S. Application Data

(60) Provisional application No. 61/930,230, filed on Jan. 22, 2014.

(51) Int. Cl.

| | | |
|---|---|---|
| *A01G 33/00* | (2006.01) | |
| *C02F 3/12* | (2006.01) | |
| *C02F 3/00* | (2006.01) | |
| *C12N 1/12* | (2006.01) | |
| *C12N 1/20* | (2006.01) | |
| *C12N 11/00* | (2006.01) | |

(52) U.S. Cl.
CPC ............... *C12N 1/20* (2013.01); *C12N 11/00* (2013.01); *C02F 3/1263* (2013.01); *C02F 3/30* (2013.01); *C02F 2003/001* (2013.01); *C02F 2303/10* (2013.01); *C02F 2305/06* (2013.01); *Y02A 40/88* (2018.01); *Y02W 10/15* (2015.05); *Y02W 10/30* (2015.05); *Y02W 10/37* (2015.05)

(58) Field of Classification Search
CPC ...... C02F 2003/001; C02F 3/30; C12N 11/11; C12N 1/20; C12N 1/12; A01G 33/00; Y02A 40/88; Y02W 10/15; Y02W 10/30; Y02W 10/37
USPC .................. 210/602, 610, 611, 631, 615
See application file for complete search history.

(56) References Cited

U.S. PATENT DOCUMENTS

2011/0159595 A1 6/2011 Mendez et al.
2013/0337518 A1 12/2013 Razavi-Shirazi et al.

OTHER PUBLICATIONS

USPTO, Written Opinion for parent PCT/US15/012332, dated Jul. 10, 2015.
Abouhend, Ahmed S., et al., "The Oxygenic Photogranule Process for Aeration-Free Wastewater Treatment", Environ. Sci. Technol. 2018, 52, (2018), 3503-3511.
Milferstedt, Kim, et al., "The importance of filamentous cyanobacteria in the development of oxygenic photogranules", Scientific Reports | 7: 17944 | DOI:10.1038/s41598-017-16614-9, (Dec. 20, 2017), 15 pgs.

\* cited by examiner

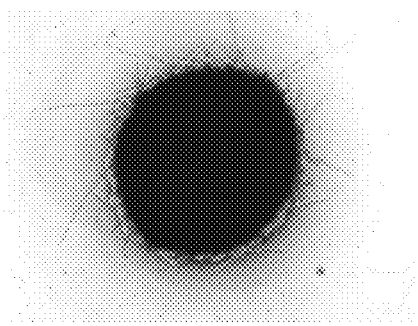
FIG. 1A          FIG. 1B
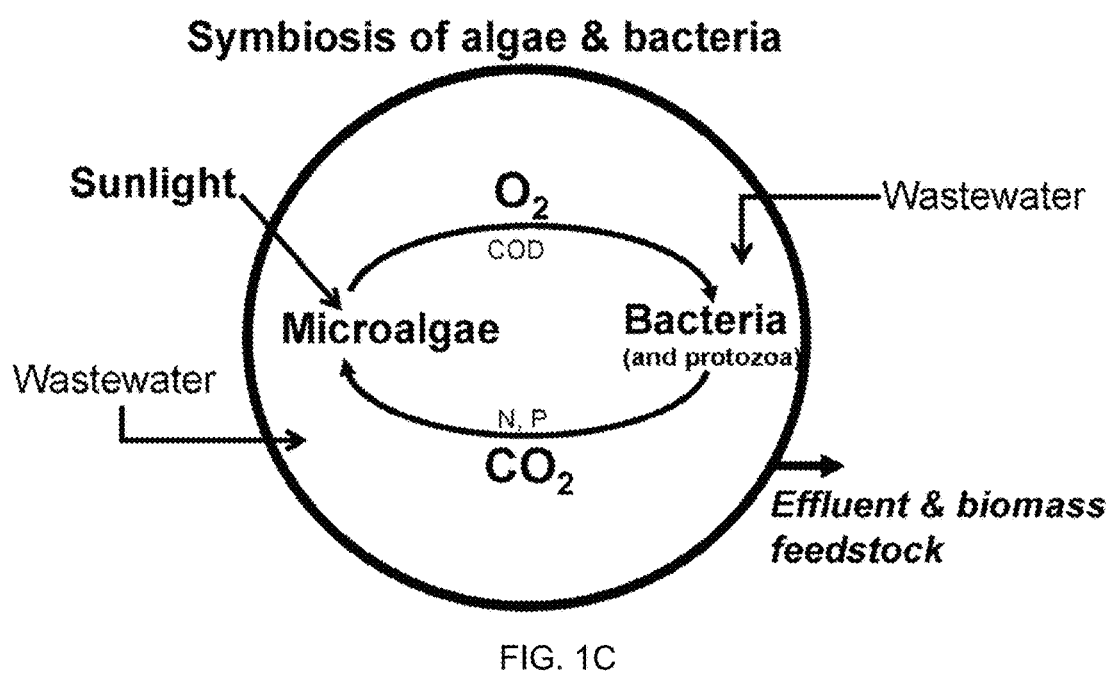
FIG. 1C

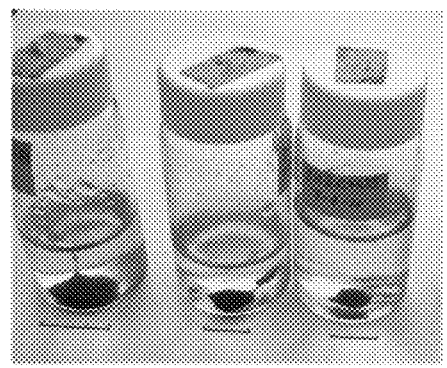
FIG. 2A　　　　　　FIG. 2B
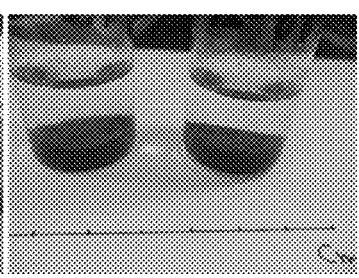
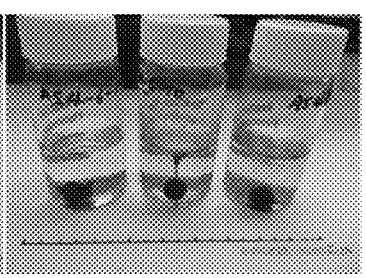
FIG. 3A　　　　FIG. 3B　　　　FIG. 3C

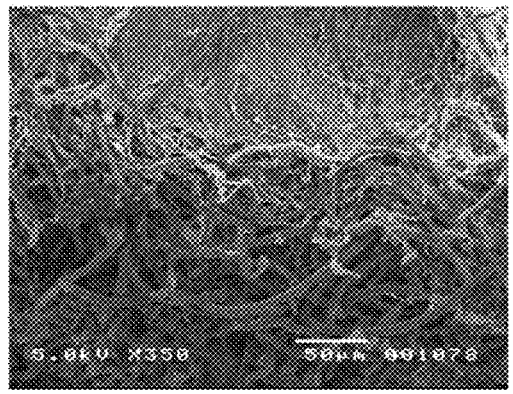
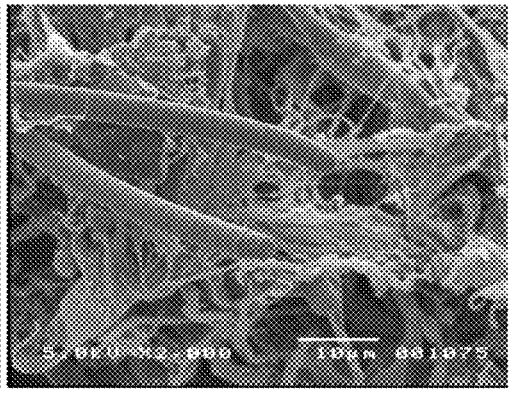
FIG. 9A              FIG. 9B
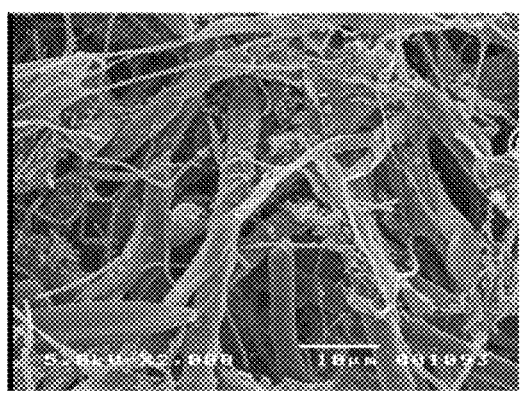
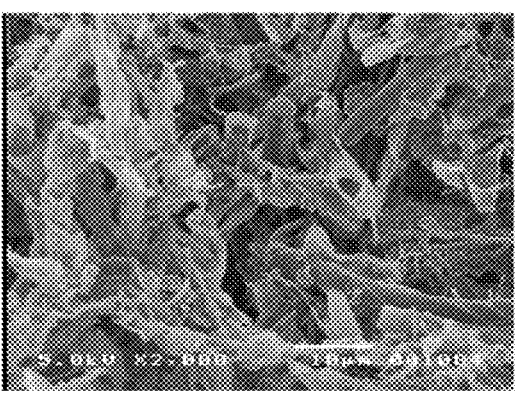
FIG. 10A             FIG. 10B

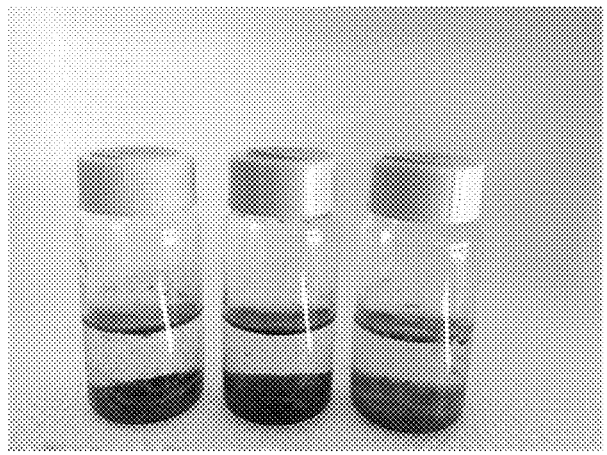 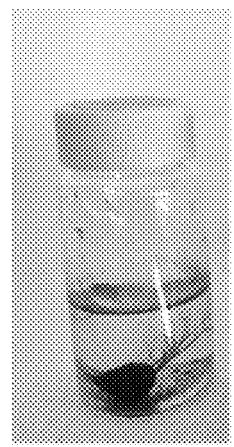
FIG. 11A  FIG. 11B
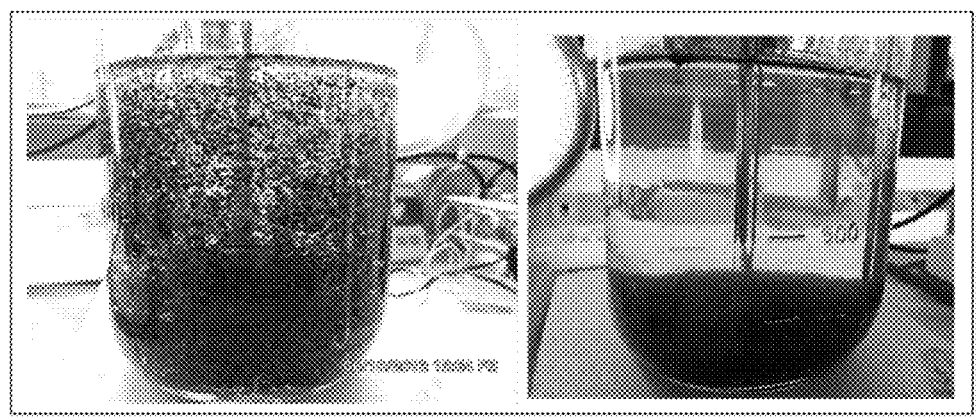
FIG. 12A  FIG. 12B

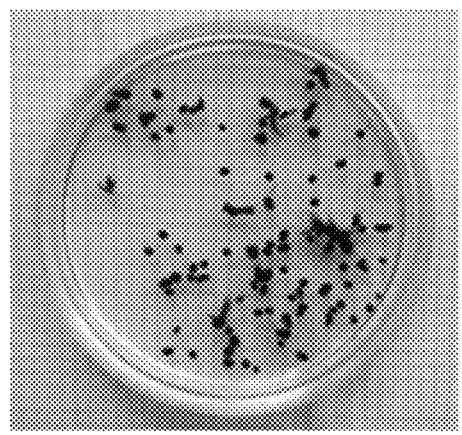
FIG. 13
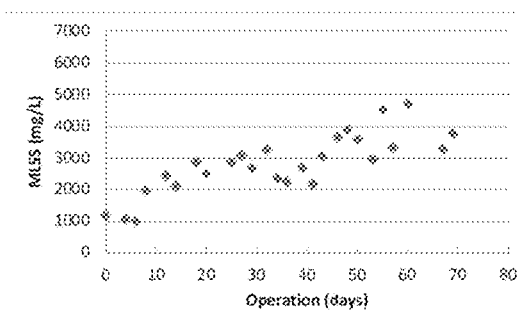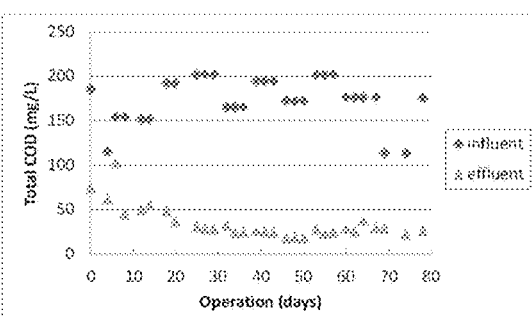
FIG. 14A　　　　　　　　FIG. 14B

ALGAL-SLUDGE GRANULE FOR WASTEWATER TREATMENT AND BIOENERGY FEEDSTOCK GENERATION

CROSS-REFERENCE TO RELATED APPLICATIONS

This application is a continuation of International Patent Application No. PCT/US15/12332 filed on Jan. 22, 2015 and claims priority to and the benefit thereof, which PCT application in turn claims priority to and the benefit of then U.S. provisional patent application Ser. No. 61/930,230, filed Jan. 22, 2014, each of which applications is incorporated herein by reference in its entirety.

FIELD OF THE INVENTION

The invention relates to wastewater treatment in general and particularly to biologically active compositions of matter that perform aspects of wastewater treatment.

BACKGROUND OF THE INVENTION

Wastewater holds great promise as a significant renewable energy resource; the energy laden in wastewater, if recovered, could provide up to 15-20% of the energy used in the U.S. The dilemma is that the primary fraction of this energy-potent material is sewage organic matter, which we use a significant amount of energy to remove, mainly by dissolving $O_2$ gas into wastewater. Currently, wastewater treatment in the U.S. consumes ~2% of energy; about 60% of this energy usage is dedicated to aeration of wastewater in the activated sludge process[1]. Algae-based wastewater treatment is gaining ground as an alternative to traditional treatment practices, because it has the potential to both, 1) treat wastewater without aeration, through the symbiotic growth of bacteria and photosynthetic microalgae (algae and cyanobacteria), and 2) preserve the chemical energy in wastewater in grown biomass. Thus, a successful microalgae process could substantially reduce energy usage for wastewater treatment and recover chemical energy from wastewater in the form of biofeedstock. However, engineering challenges limit the adoption of microalgae processes. For example, microalgae do not usually bioflocculate (naturally aggregate). The inability to bioflocculate results in ineffective separation of microalgae from water, and renders biomass recycling and harvesting, the two most important steps for bioprocess, difficult. This challenge, accompanied with the microalgae's need for light for photosynthesis, makes only certain reactor configurations, such as large open ponds, useful for microalgae processes, and they have been only limitedly used for treating wastewater in suburban and small community-based areas.

Formation of biogranules has been reported for some wastewater treatment and other bioengineered systems. One of the most well-studied biogranules is the aerobic granule sludge (AGS) that treats wastewater under aerobic conditions. It is considered that any kind of activated sludge could be developed to AGS when the growth selection pressure is met. Literature has shown that the selection pressure caused by unique process operations, such as short settling and effluent discharge times, induces the growth of activated sludge bacteria in granules, and this is the reason why AGS has been operated in a particular reactor configuration called sequencing batch reactor (SBR). The AGS process strictly depends on the artificial aeration for aerobic wastewater treatment and releases $CO_2$ into the atmosphere; thus, challenges that are inherently associated with the conventional activated sludge process are still prevalent.

There is a need for improved biologically active compositions of matter that can assist in wastewater treatment and recovery of energy from wastewater.

SUMMARY OF THE INVENTION

According to one aspect, the invention features a method of making a biologically-active granular composition of matter. The method comprises the steps of: providing a vessel configured to contain a water-based reaction medium; placing in the vessel a mixture comprising a quantity of the water-based reaction medium and at least one microalgae, the water-based reaction medium comprising material that can be consumed by a bacterium or by a protozoa present in the water-based reaction medium; incubating the mixture comprising the microalgae and the water-based reaction medium in the vessel under quiescent conditions and under at least intermittent illumination; and recovering from the incubated mixture a biologically-active granular composition of matter having both live microalgae and live bacteria present in the granular composition.

In one embodiment, the water-based reaction medium is wastewater.

In one embodiment, the water-based reaction medium is sludge.

In another embodiment, the water-based reaction medium comprises deliberately added nutrient materials.

In yet another embodiment, the deliberately added nutrient materials include organic matter.

In a further embodiment, the deliberately added nutrient materials include multivalent cations.

In still another embodiment, the illumination is varied temporally.

In a further embodiment, the illumination is varied spatially.

In yet a further embodiment, the at least one microalgae is selected from the group consisting of green algae and cyanobacteria.

In still another embodiment, the at least one microalgae comprises filamentous cyanobacteria.

In an additional embodiment, the biologically-active granular composition of matter comprises extracellular polymeric substances (EPS).

According to another aspect, the invention relates to biologically-active granular composition of matter made according to the previously described method.

According to another aspect, the invention relates to a method of wastewater remediation. The method comprises the steps of: inserting a biologically-active granular composition of matter made according to the first method described above in a wastewater treatment system; operating the wastewater treatment system under conditions that allow the biologically-active granular composition of matter to survive and generate an additional quantity of the biologically-active granular composition of matter, the wastewater treatment system receiving wastewater having a first amount of biologically-active waste per unit volume; and recovering from the wastewater treatment system processed wastewater having a second amount of biologically-active waste per unit volume, the second amount being lower than the first amount.

According to another aspect, the invention relates to a method of generating biomass. The method comprises the steps of: inserting a biologically-active granular composition of matter made according to the first method described above in a wastewater treatment system; operating the wastewater treatment system under conditions that allow the biologically-active granular composition of matter to survive and generate an additional quantity of the biologically-active granular composition of matter, the wastewater treatment system receiving wastewater having a first amount of biologically-active waste per unit volume; and recovering from the wastewater treatment system at least some of the additional quantity of the biologically-active granular composition of matter, leaving in the wastewater treatment system a sufficient amount of the biologically-active granular composition of matter to continue operation of the wastewater treatment system.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 1A is an image of an algal-sludge granule made from incubation of activated sludge.

FIG. 1B is a microscopic image of an algal-sludge granule having a diameter of 7.5 mm.

FIG. 1C is a graph illustrating the chemical processes that occur when algal-sludge granules are present in wastewater.

FIG. 2A is an image of laboratory incubation producing algal-sludge granules from activated sludge.

FIG. 2B is an image showing the general progression in biogranulation of activated sludge into algal-sludge granules (from left to right).

FIG. 3A (0 days), FIG. 3B (6 days) and FIG. 3C (25 days) are typical images showing the progress over time of algal-sludge granule growth from settled activated sludge.

FIG. 9A and FIG. 9B are SEM images of the algal-sludge granule at two magnifications.

FIG. 10A and FIG. 10B are SEM images of the algal-sludge granule showing empty slimes or slimes covering filamentous cyanobacteria.

FIG. 11A and FIG. 11B show granulation incubation experiment with activated sludge that received the addition of EDTA (0.5 mM, 1 mM, 2 mM; from left to right) and $Ca^{2+}$ (40 meq/L), respectively.

FIG. 12A and FIG. 12B are images of the bioreactor treating real wastewater, collected from the local wastewater treatment plant (Amherst, Mass.), in the laboratory during mixing and settling period, respectively.

FIG. 13 shows an image of algal-sludge granules growing in the bioreactor treating real wastewater, collected from the local wastewater treatment plant (Amherst, Mass.).

FIG. 14A and FIG. 14B show the data obtained from the bioreactor operation with real wastewater collected from the local wastewater treatment plant (Amherst, Mass.).

DETAILED DESCRIPTION

Figures 4A, 4B, 4C, 4D:
FIG. 4A (0 days), FIG. 4B (1 day), FIG. 4C (5 days), FIG. 4D (7 days), FIG. 4E (14 days), FIG. 4F (21 days), FIG. 4G (28 days), and FIG. 4H (56 days) are typical images showing the progress over time of algal-sludge granule growth from floating activated sludge.
Figures 4E, 4F, 4G, 4H:
Figures 5A, 5B, 5C:
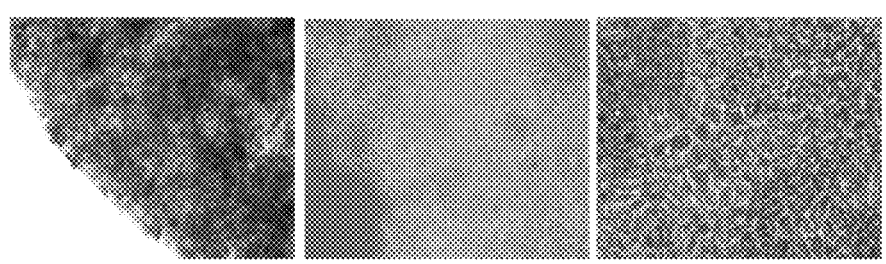
FIG. 5A (0 days), FIG. 5B (2 days) and FIG. 5C (14 days) are microscopic images of algal-sludge granules as a function of time.

A biogranule is a dense, typically, spherical aggregate of microorganisms that can be considered a self-immobilized biofilm formed in the absence of solid substratum. We produced a novel biogranule that results from transformation of activated sludge under a unique incubation condition. The novel biogranule, referred to hereinafter as an algal-sludge granule, is naturally formed (transformed naturally) from activated sludge without adding any further biological or chemical agents and composed of cyanobacteria, algae, bacteria, and protozoa within one granular biomass (See FIG. 1A-1B, FIG. 2A-2B, FIG. 3A-3C, FIG. 4A-4H, FIG. 5A-5C, FIG. 6, FIG. 7A-7D, FIG. 8A-8B, FIG. 9A-9B, FIG. 10A-10B, FIG. 11A-11B).

The cohabitation of microalgae (algae and cyanobacteria) and bacteria, and even protozoa, within the biogranule enables a consistent, efficient symbiotic wastewater treatment process: bacteria degrade organic matter, using $O_2$ produced by microalgae; in turn, microalgae harvests $CO_2$, produced from organic matter degradation, for photosynthesis. This unique biomass grows in large-size granules, typically 0.2 to 10 mm, enabling the algal-sludge granule process to perform at a high volumetric loading rate with excellent biomass separation from water, thus overcoming a major algae process challenge. See FIG. 1A-1C.

As is demonstrated herein below, we have shown that various source of wastewater sludges provide microorganisms such as algae, cyanobacteria, bacteria and protozoa that are effective in performing the methods of the invention.

The invention creates algal-sludge granules from activated sludge by incubation of activated sludge in a quiescent, batch condition illuminated with natural and/or artificial light in either an open or a closed vessel. See FIG. 1A, FIG. 2A-2B, FIG. 3A-3C, FIG. 4A-4H.

For the purposes of the present discussion, the term "quiescent", as applied to a fluid system, will be understood to mean a system in which there is no deliberate mechanical stirring, and no deliberate imposition of thermal, compositional, or density gradients that would lead to convection or other driven fluid flows that occur in a gravitational field, such as the gravitational field of the planet Earth. Note that once the granule is formed the stirring of incubation will not pose a problem. See below for further details.

The activated sludge described in this invention disclosure is referred to mixed liquor, thickened mixed liquor (also called sewage sludge, returned activated sludge, waste activated sludge), or biofilms present and used in water and wastewater treatment systems.

FIG. 2A is an image of laboratory incubation of activated sludge to produce algal-sludge granules. Activated sludge stored in the vessel could either settle or float and granulation typically proceed from that initial phase of biomass. FIG. 2B and FIG. 3A-3C are images showing the progression in biogranulation of settled activated sludge (from left to right). FIG. 4A-4H are images showing the progression in biogranulation of floating activated sludge.

The invention also involves using any photochemical treatment of activated sludge, either with or without the addition of external source of microalgae (cyanobacteria and/or green algae), to make biogranules that contain substantial numbers of microalgae (cyanobacteria and/or green algae), bacteria, and protozoa within the same granular biomass.

The novel algal-sludge granules formed from activated sludge are spherical bioaggregates, or sometimes disc-like biomass, populated with substantial numbers of microalgae (cyanobacteria and/or green algae), bacteria, and protozoa.

Figure 6:
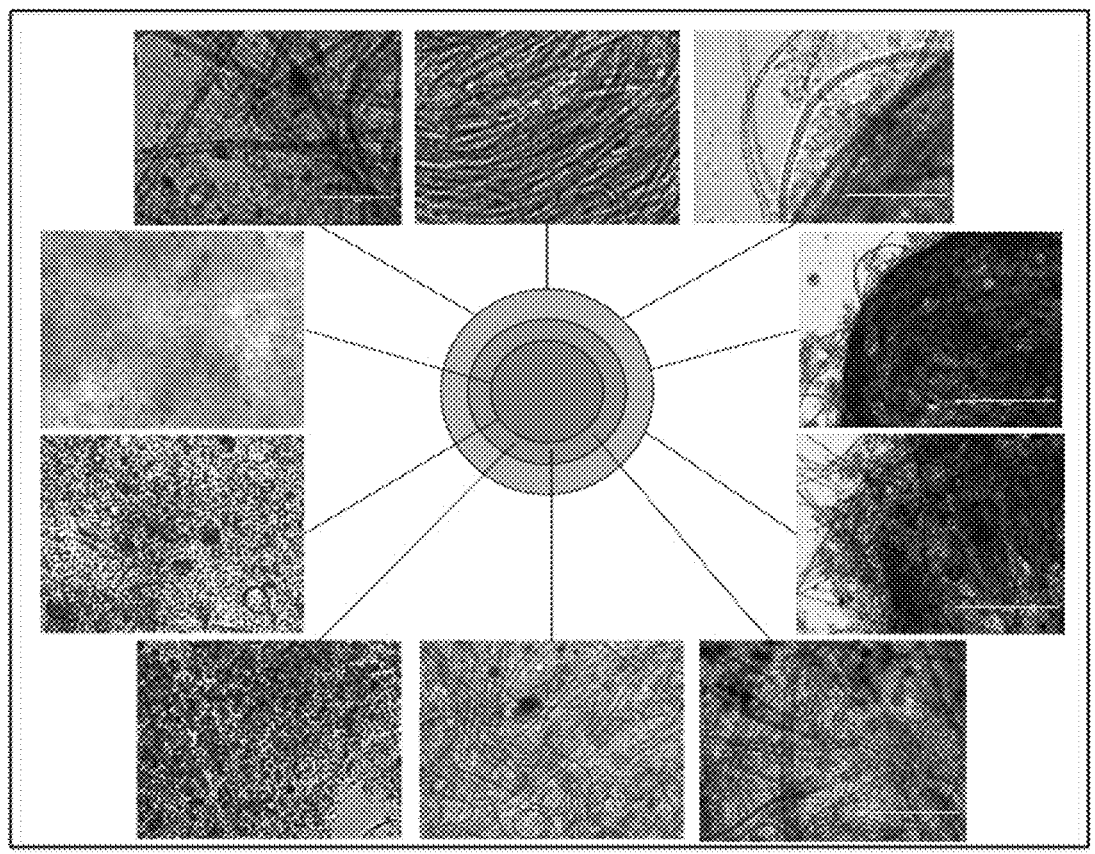
FIG. 6 shows general, overall structure of the formed algal-sludge granule with its microbial composition: outer layers are primarily composed of filamentous cyanobacteria; inner layer is composed of green algae, bacteria, and some filamentous cyanobacteria; inner center is mainly sludge-like matter.
Figure 7A:
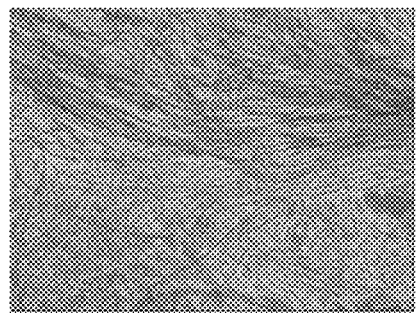
FIG. 7A, FIG. 7B, FIG. 7C and FIG. 7D are microscopic phase contrast images of the interior of algal-sludge granules showing filamentous cyanobacteria, green algae and sludge (mainly bacteria and extracellular polymeric substances).
Figure 7B:
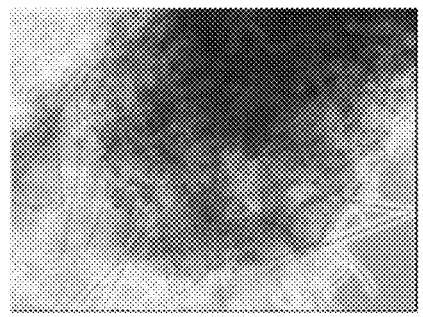
Figure 7C:
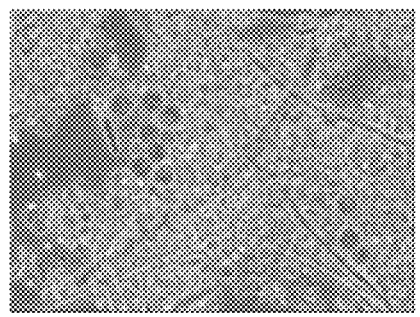
Figure 7D:
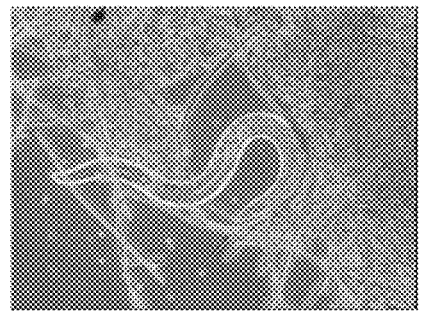

FIG. 6 depicts a typical structural composition of algal-sludge granule formed from activated sludge by our incubation method. The thick outer layer is mostly composed of motile filamentous cyanobacteria. The inner layer usually has more green algae and bacteria, with some filamentous cyanobacteria. The center of the granule is primarily composed of sludge-like matter.

Figure 8A:
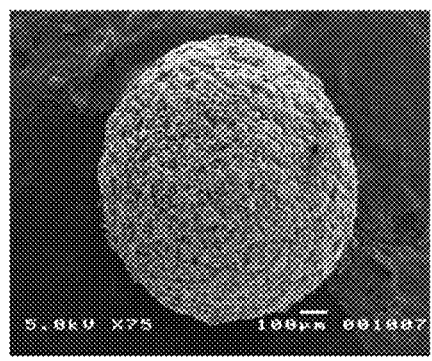
FIG. 8A is a scanning electron microscope (SEM) image of a whole algal-sludge granule.
Figure 8B:
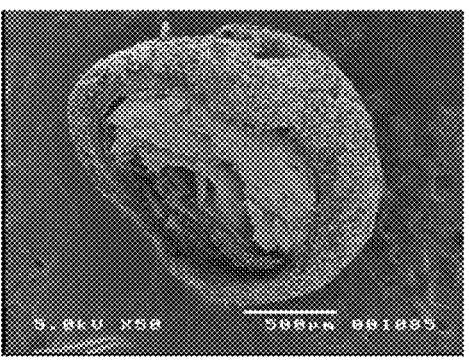
FIG. 8B is a scanning electron microscope (SEM) image of a sectioned algal-sludge granule.

FIG. 8A and FIG. 8B are scanning electronic microscopic (SEM) images of a whole and cross-sectioned granule, revealing the detailed architecture of the granule and its associated microbial composition. The settled or floating granule is not substantially different with respect to their structural and microbial composition.

The original activated sludge used to generate algal-sludge granules was typical activated sludge collected from the aeration basin at a local wastewater treatment plant (Amherst, Mass.) and did not contain measurable concentration of chlorophyll. Only microscopic analysis could inform that a very small number of algae and cyanobacteria or their cysts or spore-like materials were present within the sludge flocs. This indicates that the photochemical reaction induced substantial growth of these native cyanobacteria and algae within sludge flocs and their growth takes place along forming a unique shape of biomass, algal-sludge granules.

We conducted control experiments by incubating activated sludges under dark conditions. We did not observe the growth of algae within the stored activated sludge (thus, biomass did not change to green color) and the sludge also did not granulate. Therefore, we conclude that illumination is a driver of the process, which appears to include processes such as photosynthesis.

Our studies have shown that substantial growth of filamentous cyanobacteria, especially motile filamentous cyanobacteria, such as genus *Oscillatoria, Phormidium*, and *Microcoleus*, within sludge plays a key role in forming an overall structure of the granule and transforming sludge flocs to algal-sludge granules.

The growth of motile filamentous cyanobacteria in high-cell density in sludge is very important for granulation because their gliding motility leads to the formation of interwoven structure of cyanobacterial mat, which in our granule encompasses inner region of biomass, forming the granular structure. Small addition of EDTA into sludge completely inhibited granulation (FIG. 11A) while small addition of $Ca^{2+}$ significantly enhanced granulation (FIG. 11B). Since extracellular proteins that are involved in cell motility of many filamentous cyanobacteria are $Ca^{2+}$-dependent proteins, these results indicated that substantial growth of filamentous cyanobacteria and their motility have an important role in the formation of algal-sludge granules from activated sludge.

The novel biogranules also contain large amounts of extracellular polymeric substances (EPS) supporting granulation. Significant fractions of these EPS are slimes produced by filamentous cyanobacteria, which are essential for gliding motility of many filamentous cyanobacteria. Detection of covered slime and empty slime tubes inside the granule support this notion. See FIG. 10A and FIG. 10B.

We learned that EPS of original activated sludge is also important for granulation. Dissociation or stripping of EPS from activated sludge before incubation significantly retarded or inhibited granulation. This also indicates why flocculent nature of sludge is important for transforming activated sludge into algal-sludge granule.

The first discovery of formation of algal-sludge granules was made through incubation of activated sludge in a 20 mL scintillation vial sitting next to lab windows (under natural light conditions) for several months. Later, we incubated activated sludge in scintillation vials under artificial light conditions and also found that algal-sludge granules were generated from activated sludge.

We believe that the reason this algal-sludge granule forms in our system, but does not form in conventional water/wastewater treatment plants, is that in the incubation system we used, there is essentially no stirring of the solution. By comparison, conventional water/wastewater treatment plants deliberately pump, stir and/or aerate the water, wastewater, and/or sludge, thereby making a quiescent system effectively impossible. We believe that stirring of the system also does not promote the formation of an interwoven mat of motile filamentous cyanobacteria; thus, no effective granulation. We have discovered that once the algal-sludge granules are formed and present, stirring of the system does not pose a problem, because the algal-sludge granules are already established. The original generation of the initial algal-sludge granules, thus, requires quiescent incubation conditions.

From 2011, we have conducted many different sets of incubation experiments using activated sludge collected from six different wastewater treatment plants, and every time we confirmed granulation of activated sludge into algal-sludge granules. Our lab notebooks and electronic files include all detailed information regarding the observation about the experiments, such as photos, drawings and descriptions about the granules. The dates of each experiment set started are listed as follows:

In 2011: October 4, November 22, December 1
In 2012: February 23, April 21, November 12
In 2013: January 28, April 2, June 20, November 13

We reduced our invention to practice during our research period from October 2011 to June 2013, during which time we did not receive any Federal funds in support of this invention.

The invention is also using the original algal-sludge granules generated by the methods described above as seed or inoculum for the algal-sludge granule process in batch or any flow-through reactors. The algal-sludge granule process is mainly used for wastewater treatment, nutrient removal, recovery of resources (such as nutrients or scarce elements), production of high-value byproducts of microalgae, and/or bioenergy feedstock generation but is not limited to these purposes.

The invention is also inoculating and/or seeding offspring algal-sludge granules in the new bioreactor for the algal-sludge granule process.

This novel algal-sludge granule process could utilize natural light and/or light from the artificial lighting device to promote photosynthesis of algal-sludge granules. The process can happen under 24-hr light condition or periodic light condition by adjusting light provision. For the purpose of achieving nitrogen removal by nitrification and denitirification, the process can go under light/dark reaction, even during the day time. Also, to support the balance in the growth of microalgae and bacteria in the granule, the light condition could be adjusted. Some examples of alternating light condition of the algal-sludge granule process are shown in FIG. 15, FIG. 16 and FIG. 17.

Figure 15:
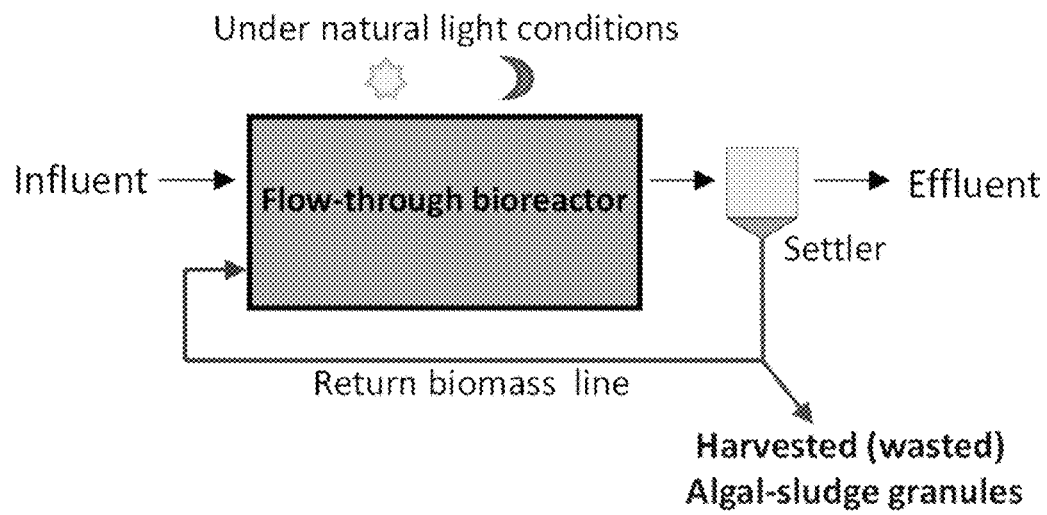
FIG. 15 is a schematic of algal-sludge granule process for wastewater treatment and nutrient removal under natural light conditions.

FIG. 15 is a schematic of algal-sludge granule process for wastewater treatment and nutrient removal under natural light conditions.

Figure 16:
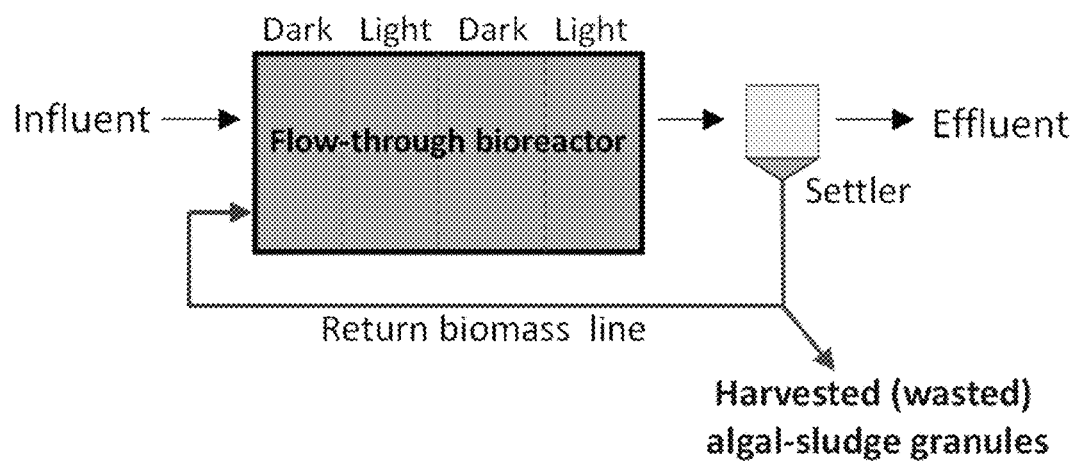
FIG. 16 is a schematic of algal-sludge granule process for wastewater treatment and nutrient removal under alternating light and dark conditions. Light conditions can be adjusted by exposing the reactor to either sunlight or artificial light. Dark conditions can be maintained by covering part of the reactor. Dark phase could be maintained with minimal aeration to support the maintenance of algae in the dark under aerobic conditions. Dark phase can also be maintained without any external source of aeration.

FIG. 16 is a schematic of algal-sludge granule process for wastewater treatment and nutrient removal under alternating light and dark conditions. Dark conditions can be maintained by covering part of the reactor. Light conditions can be adjusted by exposing the reactor to either sunlight or artificial light.

Figure 17:
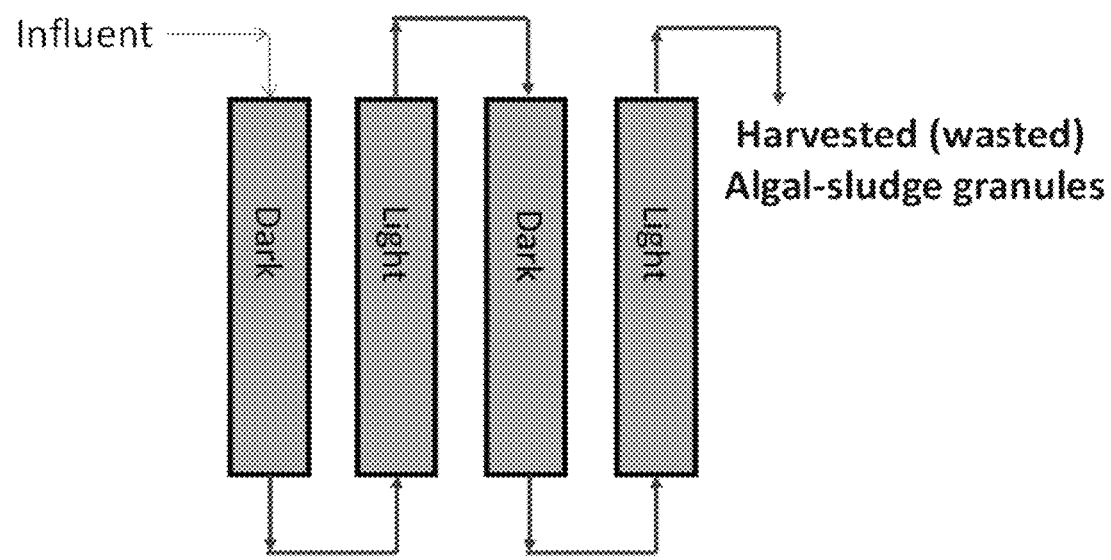
FIG. 17 is a schematic of photo-bioreactors that adopt algal-sludge granule process for wastewater treatment, nutrient removal and/or bioenergy feedstock generation. Light conditions can be different based on desired operation conditions.

FIG. 17 is a schematic of photo-bioreactors that adopt algal-sludge granule process for wastewater treatment, nutrient removal and/or bioenergy feedstock generation. Light conditions can be different based on desired operation conditions.

The algal-sludge granule process can work with or without the addition of external source of $CO_2$. The addition of $CO_2$ during the algal-sludge granule process is expected to generate more biogranular biomass, improving the yield of bioenergy feedstock.

The algal-sludge granule process can be used for the main stream, side stream (for high-strength wastewater, such as anaerobic digestion liquor), or effluent-polishing treatment for wastewater and nutrient treatment at wastewater treatment plants.

Since algal-sludge granules are large and dense, they are easily separated from treated water and wastewater, which will enable a simple biomass separation strategy, permitting a very small bioreactor and settling tank for the wastewater and nutrient treatment process. Furthermore, ultimate harvesting of algal-sludge biomass will be accelerated.

We have operated the algal-sludge granule process in sequencing batch reactors (SBRs) and found that the process can be sustained in this bioreactor application. FIG. 12A and FIG. 12B are images of the reactor set up and operation of SBR tested in the laboratory.

FIG. 13 shows an image of algal-sludge granules growing in SBR treating real wastewater collected from the local wastewater treatment plant (Amherst, Mass.)

FIG. 14A and FIG. 14B show the data obtained from the reactor operation of SBR fed real wastewater collected from the local wastewater treatment plant (Amherst, Mass.).

The invention can also be used to retrieve bioenergy from harvested algal-sludge granules by conducting physical, chemical, or biological treatment, including anaerobic digestion, of biogranules.

We believe that the biomass of algal-sludge granule itself is novel. Finding that activated sludge can be processed to create algal-sludge granules is a new discovery. As a consequence, we believe that the methods that create algal-sludge granules, which are described above, are novel. Similarly, the bioprocesses that incorporate and apply these novel algal-sludge granules for wastewater treatment, nutrient treatment, bioenergy feedstock generation, and/or other purposes are also believed to be novel.

Algal-sludge granules generate $O_2$ by themselves due to the symbiotic oxygenation from photosynthesis within the granule. The evidence of in-situ $O_2$ generation can be seen from the data shown in FIG. 18 and FIG. 19.

Figure 18A:
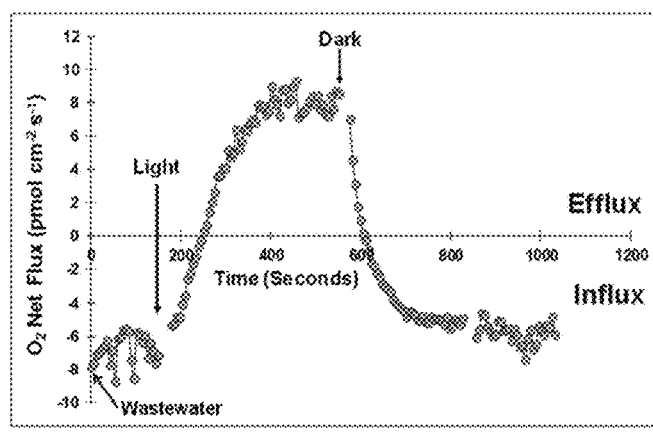
FIG. 18A is a graph of temporal changes in the flux of $O_2$ into and out of a granule.

FIG. 18A is a graph of temporal changes in the flux of $O_2$ into and out of a granule.

Figure 18B:
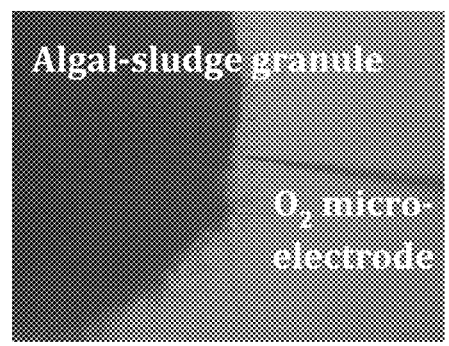
FIG. 18B is an image showing a microelectrode that measures $O_2$ at two positions about 5 μm apart within the liquid boundary layer on the exterior of an algal-sludge granule.

FIG. 18B is an image showing a microelectrode that measures $O_2$ at two positions about 5 μm apart within the liquid boundary layer on the exterior of an algal-sludge granule.

For the data shown in FIG. 18A, we measured the flux of $O_2$ very near the granule's surface. For flux measurement we used non-invasive microtest technology (NMT). As the data show, when the algal-sludge granule was placed in the new wastewater media, the $O_2$ flux was negative, indicating $O_2$ transport from solution into the granule. When light was provided, the measured net $O_2$ flux was directed outward from the granule, indicating that $O_2$ produced by photosynthesis diffused out toward the bulk liquid. Later, when the light was turned off, the flux of $O_2$ reversed immediately with the bulk $O_2$ diffusing into the granule because of continuous organic matter degradation inside the granule by sludge biomass.

Figure 19:
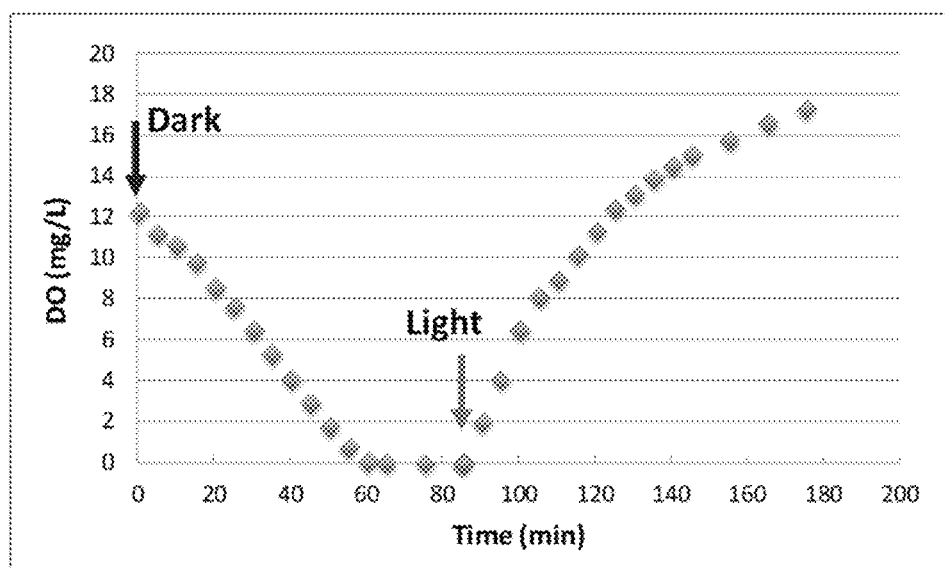
FIG. 19 is a graph of deoxygenation and reoxygenation in the bottle containing algal-sludge biogranules in response to the absence and the presence of light.

FIG. 19 is a graph of deoxygenation and reoxygenation in the bottle containing algal-sludge biogranules in response to the absence and the presence of light.

We also conducted bulk dissolved oxygen (DO) measurements in a headspace-free, closed DO bottle using biomass harvested from the SBR algal-sludge granule system (FIG. 19). The bulk DO in the reactor during the light period was supersaturated at approximately 12 mg/L. When the DO bottle containing granules was covered with aluminum foil (i.e., dark condition) the DO was consumed rapidly, indicating that photosynthesis was turned off and $O_2$ consumption by internal sludge biomass prevailed. When the same bottle was re-exposed to light there was immediate DO regeneration that reached 18 mg/L in the bottle (again, this was a closed DO bottle), indicating that photosynthesis was immediately initiated as the light was available and the granule pumped O2 into the bulk liquid, which implied that DO within the granule was also saturated.

We believe that bacteria and protozoa that cohabitate in the algal-sludge granule utilize $O_2$, produced internally by symbiotic microalgae, for organic matter removal and nutrient treatment. Thus, the algal-sludge granule process eliminates or significantly reduces the need of external aeration to dissolve $O_2$ into wastewater, which currently causes the highest energy demand at wastewater treatment plants.

Because of large size and high density, algal-sludge granules readily separate out from water, enabling a simple biomass separation strategy (small bioreactor and settler) and control of algal process, which are the biggest challenges in algal processes or algae-based wastewater treatment. In addition, symbiosis of algae and bacteria within the same granular biomass facilitates the engineering of an algae process for wastewater and nutrient treatment. Thus, algal-sludge granules and the bioprocesses that adopt these novel biogranules have great potential to achieve three important and timely outcomes, which are to: 1) treat wastewater and nutrients with minimal energy investment, 2) reduce the wastewater treatment carbon footprint, and 3) recover chemical energy laden in wastewater in the form of biofeedstock.

We are convinced that our algal-sludge granule is a novel biogranule, which also enables us to treat wastewater and nutrients and retrieve the chemical energy laden in wastewater in novel ways.

The novel algal-sludge granule process for wastewater and nutrient treatment is expected to make possible the conversion of wastewater treatment facilities to water resource recovery facilities.

REFERENCES

1. Water Environment Research Foundation. (2011) Energy production and efficiency research—the roadmap to net-zero energy. WERF Fact sheet. Alexandria, Va.
2. U.S. Environmental Protection Agency, Office of Wastewater Management. (2010) Evaluation of energy conservation measures for wastewater treatment facilities. EPA 832-R-10-005.
3. Oswald, W. J., Ludwig, H. F., Gotaas, H. B., and Lynch, V. (1951) Algae symbiosis in oxidation ponds. I. growth characteristics of *Euglena gracilis* cultured in sewage. Sewage and Industrial Wastes 23, 11.
4. Oswald, W. J., Gotaas, H. B., Ludwig H. F., and Lynch, V. (1953) Algae symbiosis in oxidation Ponds. III. photosynthetic oxygenation. Sewage and Industrial Wastes 25, 6.
5. Lavoie, A. and de la Noüe, J. (1987) Harvesting of *Scenedesmus obliquus* in wastewaters: auto- or biofloc-culation? Biotechnology and Bioengineering 30(7), 852-9.
6. Garcia, J., Hernández-Mariné, M., and Mujeriego, R. (2000) Influence of phytoplankton composition on biomass removal from high-rate oxidation lagoons by means of sedimentation and spontaneous flocculation. Water Environment Research 72, 230-237.
7. Park, J. B. K. and Craggs, R. J. (2010) Wastewater treatment and algal production in high rate algal ponds with carbon dioxide addition. Water Science and Technology 61(3), 633-639.
8. Park, J. B. K., Craggs, R. J., and Shilton, A. N. (2011) Recycling algae to improve species control and harvest efficiency from a high rate algal pond. Water Research 45(20), 6637-6649.
9. Liu, Q. S. and Liu, Y. (2008) Aerobic granulation at different carbon sources and concentrations. In: Liu, Y., Wastewater purification aerobic granulation in sequencing batch reactors. Taylor & Francis Group, LLC., Florida, pp 1-23.
10. De Kreuk, M. K. and van Loosdrecht, M. C. M (2006) Formation of aerobic granules with domestic sewage. *Journal of Environmental Engineering* 132(6), 694-697.
11. Morgenroth, E., Sherden, T., van Loosdrecht, M. C. M., Heijnen, J. J., and Wilderer, P. A. (1997) Aerobic granular sludge in a sequencing batch reactor. Water Research 31, 3191-3194.
12. Beun, J. J., van Loosdrecht, M. C. M, and Heijnen, J. J. (2000) Aerobic granulation. *Water Science and Technology* 41(5), 41-48.
13. Winkler, M.-K. H., Bassin, J. P., Kleerebezem, R., de Bruin, L. M. M., van den Brand, T. P. H., and van Loosdrecht, M. C. M. (2011) Selective sludge removal in a segregated aerobic granular biomass system as a strategy to control PAO-GAO competition at high temperatures. *Water Research* 45, 3291-3299.
14. Liu, Y. and Wang, Z. W. (2008) Selection pressure theory for aerobic granulation in sequencing batch reactors. In: Liu, Y., Wastewater purification aerobic granulation in sequencing batch reactors. Taylor & Francis Group, LLC., Florida, pp 85-110.
15. Liu, Y. Q., Liu, Y., and Tay, J. H. (2005) Relationship between size and mass transfer resistance in aerobic granules. *Letter in Applied Microbiology* 40, 312-315.
16. Beun, J. J., Heijnen, J. J., and van Loosdrecht, M. C. M, (2001) N-removal in a granular sludge sequencing batch airlift reactor. *Biotechnology and Bioengineering* 75, 82-92.
17. Liu, S. Y., Chen, Y. P., Fang, F., Xu, J., Sheng, G. P., Yu, H. Q., Liu, G., and Tian, Y. C. (2009) Measurement of dissolved oxygen and its diffusivity in aerobic granules using a lithographically-fabricated microelectrode array. *Environ Science and Technology* 43, 1160-1165.
18. Liu, Q. S. and Liu, Y. (2008) Growth kinetics of aerobic granules. In: Liu, Y., Wastewater purification aerobic granulation in sequencing batch reactors. Taylor & Francis Group, LLC. Boca Raton, Florida, pp 111-130.
19. Shepard, R. N. and Sumner, D. Y. (2010) Undirected motility of filamentous cyanobacteria produces reticulate mats. *Geobiology* 8, 179-190.
20. Hoiczyk, E. and Baumeister, W. (1997) Oscillin, an extracellular, $Ca^{2+}$-binding glycoprotein essential for the gliding motility of cyanobacteria. *Molecular Microbiology* 26, 699-708.
21. Hoiczyk, E. and Baumeister, W. (1995) Envelope structure of four gliding filamentous cyanobacteria. *Journal of Bacteriology* 177, 2387-2395.

THEORETICAL DISCUSSION

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A method comprising the steps of:
providing a vessel configured to contain a water-based reaction medium;
placing in said vessel a mixture comprising a quantity of said water-based reaction medium and at least one microalgae including filamentous cyanobacteria, said water-based reaction medium comprising material that is consumable by a live bacterium or by a live protozoan present in said water-based reaction medium;
incubating said mixture comprising said quantity of said water-based reaction medium and said at least one microalgae including said filamentous cyanobacteria in said vessel under quiescent conditions and under at least intermittent illumination such that said filamentous cyanobacteria forms a supporting matrix that incorporates said live bacterium or said live protozoan into a biologically-active bioaggregate granule; and
recovering from said incubated mixture said biologically-active bioaggregate granule.

2. The method of claim 1, wherein said water-based reaction medium is wastewater.

3. The method of claim 1, wherein said water-based reaction medium is sludge.

4. The method of claim 1, wherein said water-based reaction medium comprises deliberately added nutrient materials.

5. The method of claim 4, wherein said deliberately added nutrient materials include organic matter.

6. The method of claim 4, wherein said deliberately added nutrient materials include multivalent cations.

7. The method of claim 1, wherein said illumination is varied temporally.

8. The method of claim 1, wherein said illumination is varied spatially.

9. The method of claim 1, wherein said at least one microalgae includes green algae.

10. The method of claim 1, wherein said biologically-active bioaggregate granule comprises one or more extracellular polymeric substances.

11. The method of claim 1, wherein said water-based reaction medium comprises material that is consumable by said at least one microalgae including filamentous cyanobacteria.

12. A biologically-active bioaggregate granule made according to the method of claim 1.

13. A method of wastewater remediation, comprising the steps of:
adding one or more of said biologically-active bioaggregate granules made according to claim 1 into a wastewater treatment system;
receiving wastewater having a first amount of biologically-active waste per unit volume into said wastewater treatment system;
operating said wastewater treatment system under operating conditions that allow said one or more biologically-active bioaggregate granules to consume a portion of said biologically-active waste; and
recovering from said wastewater treatment system processed wastewater having a second amount of biologically-active waste per unit volume, said second amount being lower than said first amount.

14. The method of claim 13, wherein said operating conditions allow said one or more biologically-active bioaggregate granules to generate an additional quantity of said biologically-active bioaggregate granules.

15. A method of generating biomass, comprising the steps of:
adding one or more of said biologically-active bioaggregate granules made according to claim 1 into a wastewater treatment system;
operating said wastewater treatment system under operating conditions that allow said one or more biologically-active bioaggregate particles generate an additional quantity of said biologically-active bioaggregate granules; and
recovering from said wastewater treatment system at least some of said additional quantity of said biologically-active bioaggregate granules, leaving in said wastewater treatment system a sufficient amount of said biologically-active bioaggregate granules to continue operation of said wastewater treatment system.

16. The method of claim 1, wherein said supporting matrix comprises an interwoven support structure of said filamentous cyanobacteria.

17. The method of claim 1, wherein said biologically-active bioaggregate granule comprises an outer coating layer surrounding an inner region, the outer coating layer comprising said filamentous cyanobacteria supporting matrix.

18. The method of claim 1, wherein an inner region of said biologically-active bioaggregate granule includes at least a portion of said live bacterium or said live protozoan and a portion of said water-based reaction medium.

19. The method of claim 1, wherein said filamentous cyanobacteria is of the genus *Oscillatoria, Phormidium*, or *Microcoleus*.

20. The method of claim 1, wherein said filamentous cyanobacteria comprises at least one motile filamentous cyanobacteria.

* * * * *